(12) United States Patent
Leckenby et al.

(10) Patent No.: US 9,655,813 B2
(45) Date of Patent: May 23, 2017

(54) STYLUS AND TREATMENT HEAD FOR USE WITH A MEDICAL DEVICE

(75) Inventors: Stephen Leckenby, Victoria (CA); Adam Looker, Berlin (DE); Augustus Mercer, Victoria (CA); Trevor Moat, Victoria (CA)

(73) Assignee: KKT International Ltd. (BB)

( * ) Notice: Subject to any disclaimer, the term of this patent is extended or adjusted under 35 U.S.C. 154(b) by 775 days.

(21) Appl. No.: 13/994,098

(22) PCT Filed: Dec. 8, 2011

(86) PCT No.: PCT/IB2011/055536
§ 371 (c)(1),
(2), (4) Date: Jun. 13, 2013

(87) PCT Pub. No.: WO2012/080910
PCT Pub. Date: Jun. 21, 2012

(65) Prior Publication Data
US 2013/0267876 A1 Oct. 10, 2013

Related U.S. Application Data

(60) Provisional application No. 61/422,893, filed on Dec. 14, 2010, provisional application No. 61/547,853, filed on Oct. 17, 2011.

(51) Int. Cl.
*A61B 5/103* (2006.01)
*A61H 99/00* (2006.01)
(Continued)

(52) U.S. Cl.
CPC ............. *A61H 99/00* (2013.01); *A61B 17/29* (2013.01); *A61H 1/008* (2013.01); *A61B 90/30* (2016.02);
(Continued)

(58) Field of Classification Search
CPC ...... A61B 5/4528; A61B 5/103; A61B 5/0053
(Continued)

(56) References Cited

U.S. PATENT DOCUMENTS

| 4,800,878 A | 1/1989 | Cartmell |
| 5,275,593 A * | 1/1994 | Easley ............... A61F 9/008 604/27 |

(Continued)

FOREIGN PATENT DOCUMENTS

| CA | 2521344 | 3/2006 |
| WO | WO2009009220 | 1/2009 |

OTHER PUBLICATIONS

International Search Report, for International Application No. PCT/IB2011/055536, completed Apr. 3, 2012.
(Continued)

*Primary Examiner* — Daniel Cerioni
(74) *Attorney, Agent, or Firm* — Westberg Law Offices

(57) ABSTRACT

A stylus and a treatment head for use with a medical device for imparting a force is provided. The stylus allows a practitioner to maintain focus on the treatment location while adjusting placement and force. This is because a light signal is emitted in the vicinity of the distal end of the stylus, proximate the treatment location on the patient. Alternatively, an audible or a tactile signal is employed for feedback. As a safety feature, the stylus is provided with means to allow it to collapse at forces above the acceptable limit.

13 Claims, 7 Drawing Sheets

(51) Int. Cl.
*A61B 17/29* (2006.01)
*A61H 1/00* (2006.01)
A61H 23/02 (2006.01)
A61B 90/30 (2016.01)
A61B 90/00 (2016.01)

(52) U.S. Cl.
CPC . *A61B 2017/2931* (2013.01); *A61B 2090/065* (2016.02); *A61H 23/02* (2013.01); *A61H 2201/0173* (2013.01); *A61H 2201/0188* (2013.01); *A61H 2201/1253* (2013.01); *A61H 2201/5048* (2013.01); *A61H 2201/5061* (2013.01)

(58) Field of Classification Search
USPC ............................................. 600/587
See application file for complete search history.

(56) References Cited

U.S. PATENT DOCUMENTS

| | | | |
|---|---|---|---|
| 5,447,491 A | 9/1995 | Bellandi | |
| 5,589,639 A | 12/1996 | D'Antonio et al. | |
| 5,611,805 A | 3/1997 | Hall | |
| 5,618,315 A * | 4/1997 | Elliott | A61H 23/0218 601/108 |
| 6,190,339 B1 | 2/2001 | Imazaike | |
| 6,200,282 B1 | 3/2001 | Furuie | |
| 6,304,712 B1 | 10/2001 | Davis | |
| 6,585,668 B2 | 7/2003 | Nissim | |
| 6,655,597 B1 * | 12/2003 | Swartz | G06K 7/10574 235/462.45 |
| 6,739,744 B2 | 5/2004 | Williams | |
| 6,969,384 B2 | 11/2005 | de Juan, Jr. | |
| 7,714,239 B2 | 5/2010 | Smith | |
| 2004/0092927 A1* | 5/2004 | Podhajsky | A61B 18/1402 606/42 |
| 2006/0184167 A1* | 8/2006 | Vaska | A61B 17/2202 606/41 |
| 2006/0217596 A1 | 9/2006 | Williams | |
| 2007/0135735 A1 | 6/2007 | Ellis | |
| 2009/0223300 A1 | 9/2009 | Lapstun et al. | |
| 2010/0049126 A1* | 2/2010 | Bronfeld | A61B 5/1405 604/113 |
| 2010/0137845 A1 | 6/2010 | Ramstein | |
| 2011/0160556 A1 | 6/2011 | Govari | |

OTHER PUBLICATIONS

Written Opinion of the International Searching Authority, for International Application No. PCT/IB2011/055536, completed Apr. 3, 2012.

* cited by examiner

STYLUS AND TREATMENT HEAD FOR USE WITH A MEDICAL DEVICE

This application is a National Stage of International Application No. PCT/IB2011/055536, International Filing Date: Dec. 8, 2011, which claims the benefit of U.S. Provisional Application No. 61/422,893, filed Dec. 14, 2010, and U.S. Provisional Application No. 61/547,853, filed Oct. 17, 2010. The entire contents of each of the above-identified prior applications are hereby incorporated by reference.

TECHNICAL FIELD

The technology relates to a stylus and treatment head for use with a medical device that imparts a force on a patient. More specifically, the technology is a stylus having a point-of-treatment visual output to inform a practitioner of the force imparted through the stylus.

BACKGROUND ART

Numerous medical devices are provided with means to illuminate the working area and the relevant sections of the device. For example, US Publication Number 20060217596 discloses illuminated surgical retractors including at least one retractor blade and a light delivery system. The light delivery system may include an array of lights which may be attached directly to the retractor blade or to a support in the shape of an elongated blade that extends along the length of the retractor blade for illuminating all or a portion of the length of the retractor blade. In one embodiment the light delivery system is in the form of a light rod which emits light at a distal end.

U.S. Pat. No. 6,739,744 discloses a lighting device that includes an optic light guide having a free end that emits directional light. Surrounding the free end is a sleeve having an aperture through which a beam of light emitted by the free end of the light guide passes. The sleeve may be moved in and out relative to the free end to vary the size of the beam of light passing through the aperture.

U.S. Pat. No. 6,304,712 discloses a bendable medical, dental and surgical illuminating appliance that includes a light-conducting rod, at least a portion of which is light projecting. The rod is flexible and comprises a self-sustaining shape. The rod also includes a light inlet that is operably engaged with the outlet of a fiberoptic conductor.

With regard to force sensors, U.S. Pat. No. 7,714,239 discloses a mechanical force switch to be disposed along a longitudinal device axis of a medical device that includes an electrically conductive switching piston to form a first electrical contact of the switch, a hollow body, an end stop, a bias device, and an electrically conductive second contact of the switch electrically insulated from the piston. The piston is movably disposed in the body hollow along the axis to define different switch-making and -breaking positions. The bias device surrounds the piston and imparts bias against it to retain it in one of the two positions until an external axis force overcomes the bias, at which time the switch indicates a state changeover. The switch can be normally open or closed. Electrically coupled to the switch is an indicator light which illuminates in response to one of the two positions, either opened or closed. It is also contemplated that if the force switch is provided with a strain gauge, also referred to as a load cell, then a continuous force output can be displayed to the user in which, for example, a row of light emitting diodes (LEDs) gradually light up dependent upon the amount of force or an LCD or LED numerical field increments numerical values corresponding to the amount of force imparted through the force switch.

With regard to an applicator having multiple probes or contact points, U.S. Pat. No. 6,585,668 discloses a massage head comprising robot massage hands that are distinctly anthropomorphic. Each robot massage hand comprises an articulated thumb and three articulated fingers, in accordance with a preferred embodiment of the present invention. Robot massage hands can perform finer and more varies motions than robot massage hands. For example, robot massage hands can perform pinching and grasping motions substantially more similar to pinching and grasping motions performed by the human hand than pinching and grasping motions performed by robot massage hands.

Similarly, U.S. Pat. No. 6,200,282 discloses a machine that comprises a massage unit having a first therapeutic finger for giving tapping massage to the upper part or the upper to frontal part of the shoulder of the user, and a second therapeutic finger for giving tapping massage to the back or the back to the posterior part of the shoulder. The fingers each have a portion to be brought into contact with the user at the forward end of an arm. The arms are pivotally movable independently of each other by respective finger drive means. U.S. Pat. No. 6,190,339 also discloses a massage machine. In this case, the massage device has first and second massage members. The first massage member performs a circulating motion including (i) a massage zone where the member approaches the second massage member in a locus which swells in an outward direction as seen from a massage arm; and (ii) a release zone where the member separates from the second massage member in a locus which is shorter than the massage zone. The second massage member performs a reciprocal rocking motion in synchronization with the first massage member.

While the foregoing examples all attempt to mimic the motion of a human hand giving a massage, other devices simply have multiple probes that provide a repetitive force. In this regard, U.S. Pat. No. 5,447,491 is exemplary. It discloses an anticellulitis massaging device comprising a plurality of massaging elements or fingers located within a body member or casing and susceptible of axial percussion movements and oscillating and/or rotating movements, which are controlled by a motor assembly and via cam actuating means.

DISCLOSURE OF INVENTION

Technical Problem

Controlling and monitoring force exerted on a patient during treatment

Technical Solution

When applying a force to a patient, it is important to ensure that the force is within the prescribed limits. As the force applied is often controlled by the relative position of the device and this is often electronically controlled, one can see how easy it would be to position the device such that the force is outside of the desired range. Ideally, therefore, a practitioner would be able to receive feedback with regard to the force being exerted during the positioning step and would not have to shift their gaze between the treatment location and a remote output in order to do so. The present technology provides a stylus that allows a practitioner to focus on the treatment location while positioning the stylus on the patient and adjusting the force. One way to achieve this goal is to have an indicator proximate to the treatment location. Light pipes, fibre optics and lights located at the distal end of the stylus all permit the practitioner to receive feedback in the form of a light signal without removing their gaze from the vicinity of the area to be treated. An alternative approach is to provide the stylus with an audible signal. Yet another approach is a tactile signal, for example, a vibration. These signals identify when the stylus load is too low, is in the appropriate range, and when it is too high, whether in compression or tension. An additional use of the technology is as a measure of tension or compression in relation to preset values.

In the preferred embodiment, the stylus is a light pipe. At least the tip, which is located at the distal end, scatters light, and therefore is readily visible to the practitioner at the treatment location or very close to the treatment location, regardless of the viewing angle. By using light emitting diodes controlled by a Red Green Blue (RGB) controller, the colour injected into the light pipe switches from blue, which is associated with forces below the desired range, to green, which is associated with forces within the desired range, to red, which is associated with forces greater than acceptable range. The stylus has a load cell at a proximal end that measures the force exerted during treatment. If the load exceeds the acceptable limits, mechanical features in the stylus assembly collapse, thereby preventing excess force from being applied through the stylus. Preferably, this is at a force much higher than the limits used for treatment, in other words, much higher than a force that causes the light to be red.

In an alternative embodiment, a treatment head for use in medical applications is provided wherein force is applied at a treatment location. The treatment head comprises:

A treatment head for use in medical applications wherein force is applied at a treatment location, the treatment head comprising:
  i) a distal end;
  ii) a proximal end, the proximal end having a strain gauge;
  iii) a shaft between the distal end and the proximal end, the shaft comprising a rod, an inner sleeve for retaining the rod, an outer sleeve and means for generating a magnetic field therebetween, such that in use, the inner sleeve and outer sleeve are releasably attached to one another until a force limit is reached, at which force, the magnetic field is broken resulting in collapse of the treatment head;
  iv) an applicator located on the rod, the applicator comprising: an at least one tip, the tip being adjustable distally, proximally and orthogonally in relation to the shaft of the rod; and
  v) a signaler in electrical communication with the strain gauge.

Preferably the rod is a light pipe and the signaler is a light source and a light controller, such that in use, a light signal is emitted in the vicinity of the treatment location in response to a predefined force or a range of predefined forces.

It is advantageous that the applicator comprises at least two tips and the treatment head is configured to provide the same force at each tip.

Uses of the stylus and treatment head in force imparting devices are also provided. These devices are preferably medical devices.

DESCRIPTION OF DRAWINGS

FIGS. 2 and 2a are longitudinal mid-section views of the shaft of the present technology wherein FIG. 2 shows the placement of the magnets or magnet and magnetic material for compression and FIG. 2a shows the placement of the magnets for tension.

MODE FOR INVENTION

Definitions:

Resistant in the context of the present technology is meant to mean any material that is capable of transferring a force axially.

Light transmitting material in the context of the present technology is meant to mean a transparent or translucent material.

Resilient in the context of the present technology is meant to mean any material that is able to be repeatedly deformed and returned to its original form.

Treatment location in the context of the present technology is meant to mean at or in the vicinity of the location on a patient being treated.

Signaler in the context of the present technology produces at least one of a tactile, audible or visual signal.

DETAILED DESCRIPTION

Figure 1:
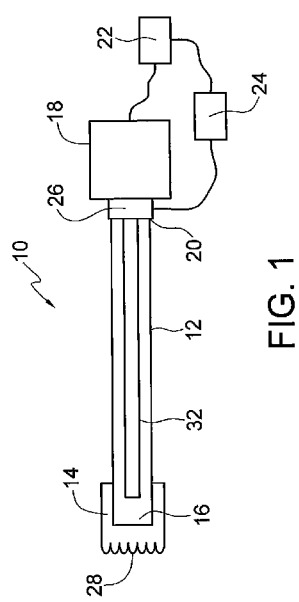
FIG. 1 is a longitudinal mid-section view of the stylus of the present technology.

As shown in FIG. 1, a stylus for imparting a force or measuring a force on a patient is generally referred to as 10. The stylus 10 is for use with a medical device for imparting a force, either tensile or compressive. The stylus 10 has a tip 14 at a distal end 16, a strain gauge 18 at a proximal end 20 and a shaft 12 therebetween. The contact area of each tip 114 is preferably about 0.8 cm in diameter to about 1.2 cm in diameter, more preferably about 0.9 cm in diameter to about 1.1 cm in diameter and most preferably 1 cm in diameter. The strain gauge 18 is in electrical communication with a controller 22 and a light controller 24, the light controller 24 being in electrical communication with a light source 26. The strain gauge 18 is preferably a load cell. The light source 26 is preferably a light emitting diode (LED) light source. The LED light source is preferably an RGB LED with independent inputs for generating red, green, and blue light.

Figure 2:
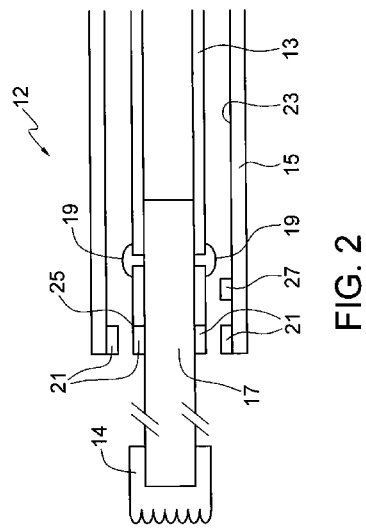
Figure 2A:
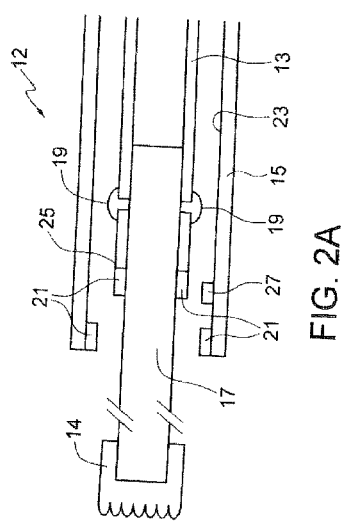

As shown in FIGS. 2 and 2a, the shaft 12 consists of an inner sleeve 13, an outer sleeve 15 and a rod 17. The rod 17 is attached to the inner sleeve 13, for example by a friction fit, using a pair of positioning screws 19. The inner sleeve 13 and the outer sleeve 15 are releasably held to one another by electromagnets 21. As shown in FIG. 2, perimeter magnets 21 are located on the inner surface 23 of the outer sleeve 15 and in the vicinity of the end 25 of the inner sleeve 13 when the device is used for compressive forces. Magnets 21 are also located on the inner sleeve 13 in the vicinity of the end 25. As shown in FIG. 2a, when used in tension, the perimeter magnets 21 are located on the inner surface 23 of the outer sleeve 15 distal to the end 25 of the inner sleeve 13. Magnets 21 are also located on the inner sleeve 13 in the vicinity of the end 25. A sensor 27 provides electronic feedback to signal when the magnetic connection is broken.

Figure 3:
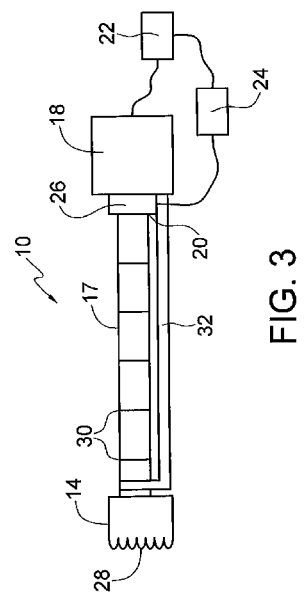
FIG. 3 is a longitudinal view of an embodiment of the technology of FIG. 1.

The rod 17 is resistant and light transmitting. In one embodiment it is preferably an acrylic rod that functions as a light pipe. The rod 17 is preferably provided with light scattering segments 30 as shown in FIG. 3. In the preferred embodiment, the light scattering segments 30 are facets that provide rings of light spaced along the rod 17. Light scattering may be provided by etching or by machining or other methods as would be known to one skilled in the art. The tip 14 also preferably scatters light. The tip 14 is preferably releasable to allow for it to be replaced between patients. If the tip 14 is used to impart a force, it is preferably a resilient or resistant material, and may be translucent in and of itself, without further treatment, such as etching. The tip may further be provided with protrusions 28, dimpling or other surface contouring. If additional strength is required, a slave 32 is placed in parallel with the shaft 12, either as a core as shown in FIG. 1 or directly adjacent, as shown in FIG. 3.

Figure 4:
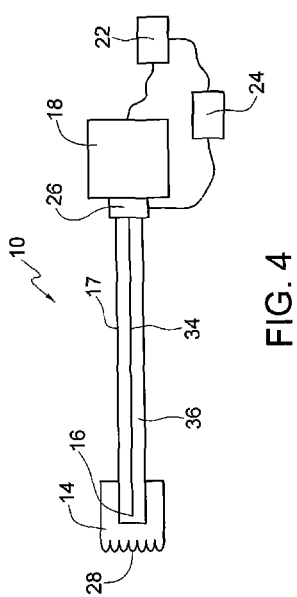
FIG. 4 is a longitudinal mid-section view of an alternative embodiment of the technology of FIG. 1.

As shown in FIG. 4, in another embodiment, the rod 17 is a fibre optic conductor 34 encased in a resistant housing 36. The tip 14, which preferably releasable, fits over the distal end 16, and scatters light. If the tip 14 is used to impart a force, it is preferably a resilient material, and may be translucent in of itself, without further treatment, such as etching.

Figure 5:
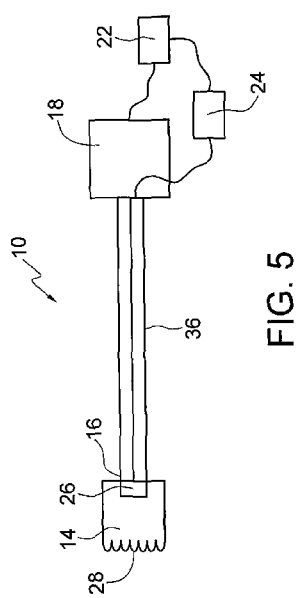
FIG. 5 is a longitudinal view of an alternative embodiment of the technology of FIG. 1.

In another embodiment, the stylus 10 is provided with a light source 26 in the vicinity of the distal end 16, as shown in FIG. 5. The light source 26 is in electrical communication with the light controller 24 and a resistant housing 36 is employed that functions as the rod 17.

Figure 7:
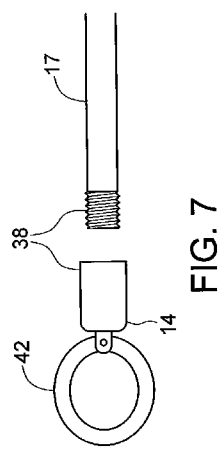
FIG. 7 is an exploded longitudinal view of an alternative embodiment of the tip.
Figure 6:
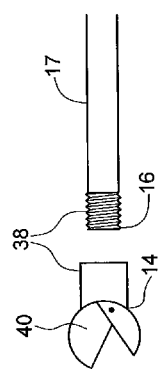
FIG. 6 is an exploded longitudinal view of the tip and distal end of the stylus of FIG. 1.

The tip 14 may be configured to provide tension. In this mode, a releasable locking mechanism 38 retains the tip 14 on the stylus 10, as shown in FIG. 6. This may be any mating pair, such as, but not limited to, a threaded pair, or a key and keyway. The tip 14 is provided with a grip 40 as shown in FIG. 6. In alternative embodiments, the grip can be replaced with a loop 42 or tether as shown in FIG. 7. When the stylus 10 is used to produce tension, the stylus 10 need not be resistant. Therefore, for example, a bendable housing can be used with fibre optic conductor or electrical cord. Similarly, a bendable, light transmitting polymeric material can be used as the light pipe. Further, the load cell can be configured to measure tension and compression alternately; in other words, the device could measure tension and compression without any changes to hardware. In this case, the light assignments could be changed to reveal polarity of stylus force (blue for compression, red for tension, green for neither, for example, but not limited to) with either light intensity or hue (obtained by colour intensity mixing) corresponding to magnitude. For this case, a combination of the two collapse mechanisms can be used to ensure forces beyond compressive or tensile limits for an application are not exceeded.

Note too that intensity could be relayed to the operator by flash rate of the LEDs. Humans can generally detect flicker rates up to about 20 Hz, so, for example, but not limited to, DC (steady output) might indicate no applied force; 1 Hz (one flash per second) might indicate 10% of limit, 2 Hz 20%, and so forth, in either direction as indicated by light colour.

When used with a medical apparatus for imparting a compressive force, the stylus 10 collapses at a force commensurate with an upper limit. The stylus 10 collapses as follows: When the force exceeds the acceptable limit, the magnets 21 are forced apart. Once the magnetic connection (magnetic field) has been broken, the inner sleeve 13 and the outer sleeve 15 lose compliance with one another and are free to move independently. As the magnetic field decreases at a strength that is the square of distance, once the field is broken, the two sleeves 13, 15 telescope readily in response to the force. An electronic feedback then can signal to stop movement of the device and further, can signal to retract the device away from the patient, and further, indicate to the controller and ultimately the operator that the maximum force limit was reached. If the stylus 10 is used for impulse treatment, the electronic feedback can also signal to stop the movement of the stylus 10. The load cell 18 provides an additional feedback to assist in keeping the operating conditions within the acceptable working range. In one example the working range, when the compressive force is for application to bone, will be less than about 5 pounds, more preferably less than about 4 pounds and most preferably less than about 2.5 pounds (about 22 N, about 18 N and about 11 N, respectively) and the upper limit will be about 5 pounds, more preferably about 4 pounds and still more preferably about 3 pounds. When used with a medical device to measure compressive force, the stylus 10 need not be set to collapse at a force commensurate with an upper limit, however, it is preferable to do so. Similarly, when used with a medical device for imparting tension, the stylus 10 is set to collapse at a force commensurate with an upper limit. When used with a medical device to measure tension, the stylus 10 need not be set to collapse at a force commensurate with an upper limit, however, it is preferable to do so.

The LED light source 26 is preferably controlled by a red green blue (RGB) LED light controller 24 or any other additive light controller 24. This allows for a variety of colours, modes and intensities as the light signal.

When used in the compressive force mode, the upper limit is set and the stylus 10 is located on the patient as needed. The force to be applied is controlled by the controller 22. As the practitioner increases the force, the LED light source 26 emits light to indicate the force level. In one embodiment, the light signal is a flashing signal having a decreasing or increasing period, with either 'on', 'flashing' or 'off' indicating the working load. In another embodiment, light intensity is used to indicate the load. In another embodiment the colour is used to indicate the load. In yet another embodiment, any combination of light intensity, colour, or pulse can be indicative of the force. Should the force exceed the set upper limit, the stylus 10 collapses. Preferably, collapse of the stylus 10 triggers the controller 22 to retract the medical device, thereby retracting the stylus 10 from the patient.

When used to measure a compressive force, the upper limit is set and the stylus 10 is located on the patient as needed. The force to be applied is controlled by the patient and measured by the load cell. As the force increases, the LED light source 26 emits light to indicate the force level. In one embodiment, the light signal is a flashing signal having a decreasing or increasing period, with either 'on', 'flashing' or 'off' indicating the working load range. In another embodiment, light intensity is used to indicate the load. In another embodiment the colour is used to indicate the load. The light emitted is preferably blue at low force, green at an acceptable predetermined force or range of predetermined forces, and red at any force above the acceptable range. For example, for the treatment of cervical vertebrae, blue light will be emitted when the force is less than about 4 ounces (1.11 N) and more preferably less than about 2 or 3 ounces (0.556 N or 0.834 N) and most preferably less than about 1 ounce (0.278 N). Green light will be emitted when the force is between about 4 and 6 ounces (1.11 N and 1.668 N), more preferably between about 2 or 3 ounces (0.556 N or 0.834 N) and 5 ounces (1.39 N) and most preferably between about 1 and 3 ounces (0.278 N and 0.834 N). Red light will be emitted when the force is more than about 6 ounces (1.668 N, more preferably more than about 5 ounces (1.39 N) and most preferably more than about 3 ounces (0.834 N). In yet another embodiment, any combination of light intensity, colour, or pulse can be indicative of the force. Should the force exceed the set upper limit, the stylus 10 collapses.

When used in the tension mode, the upper limit is set and the tip is releasably attached to the patient as needed. The force to be applied is controlled by the controller 22. As the practitioner increases the force, the LED light source 26 emits light to indicate the force level. In one embodiment, the light signal is a flashing signal having a decreasing or increasing period, with either 'on', 'flashing' or 'off' indicating the working load. In another embodiment, light intensity is used to indicate the load. In another embodiment the colour is used to indicate the load. In yet another embodiment, any combination of light intensity, colour, or pulse can be indicative of the force. Should the force exceed the set upper limit, the stylus 10 collapses.

When used to measure tension, the upper limit on the load cell 18 is set and the tip is releasably attached to patient as needed. The force to be applied is controlled by the patient and measured by the load cell. As the patient increases the force, the LED light source 26 emits light to indicate the force level. In one embodiment, the light signal is a flashing signal having a decreasing or increasing period, with either 'on', 'flashing' or 'off' indicating the working load. In another embodiment, light intensity is used to indicate the load. In another embodiment the colour is used to indicate the load. In yet another embodiment, any combination of light intensity, colour, or pulse can be indicative of the force. Should the force exceed the set upper limit, the stylus 10 collapses.

In an alternative embodiment, there is an audio feedback using a speaker, such as a piezoelectric speaker, in communication with the load cell. This allows for the practitioner to remain focused on the treatment location without having to check outputs remote to the patient. It also addresses the case where the practitioner is colour-blind, or blind altogether.

In another alternative embodiment, there is a tactile feedback whereby vibration is used to indicate the force and therefore a vibrator is in communication with the load cell. Again this allows the practitioner to remain focused on the treatment location without having to check outputs remote from the patient. The vibration may also be detected as an audible signal.

Figure 8:
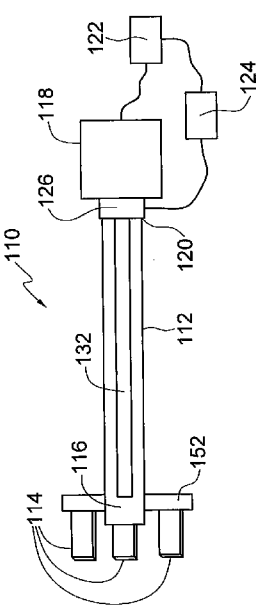
FIG. 8 is a longitudinal mid-section view of the treatment head of the present technology.

In yet another embodiment as shown in FIG. 8, a head for imparting a force at more than one point on a patient is generally referred to as 110. The head 110 is for use with a medical device for imparting a force, either tensile or compressive. The head 110 has from two to five tips (contact points) 114 at a distal end 116, a strain gauge 118 at a proximal end 120 and a shaft 112 therebetween. The contact area of each tip 114 is preferably about 0.8 cm in diameter to about 1.2 cm in diameter, more preferably about 0.9 cm in diameter to about 1.1 cm in diameter and most preferably 1 cm in diameter. The strain gauge 118 is in electrical communication with a controller 122 and optionally a light controller 124, the light controller 124 being in electrical communication with a light source 126. The strain gauge 118 is preferably a load cell. The optional light source 126 is preferably a light emitting diode (LED) light source. The LED light source is preferably an RGB LED with independent inputs for generating red, green, and blue light. For two tips 114, blue light will be emitted when the force is less than about 8 ounces (2.22 N) and more preferably less than about 4 or 6 ounces (1.22N or 1.668N) and most preferably less than about 2 ounces (0.556 N). Green light will be emitted when the force is between about 8 and 12 ounces (2.22 N and 3.336 N), more preferably between about 4 or 6 ounces (1.22 N or 1.668 N) and 10 ounces (2.78 N) and most preferably between about 2 and 6 ounces (0.556 N and 1.668 N). Red light will be emitted when the force is more than about 12 ounces (3.336 N, more preferably more than about 10 ounces (2.78 N) and most preferably more than about 6 ounces (1.668 N). For three tips, the values will be half again as much. In yet another embodiment, any combination of light intensity, colour, or pulse can be indicative of the force. Should the force exceed the set upper limit, the stylus 10 collapses.

Figure 9:
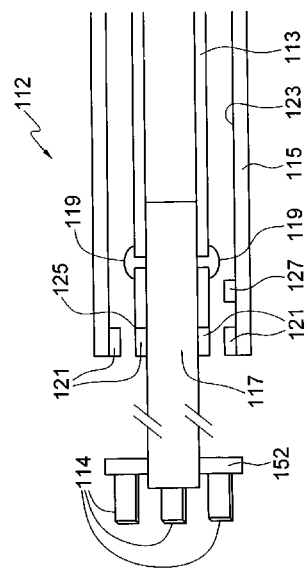
FIG. 9 is a longitudinal mid-section view of the shaft of the present technology showing the placement of the magnets or magnet and magnetic material.

As shown in FIG. 9, the shaft 112 consists of an inner sleeve 113, an outer sleeve 115 and a rod 117. The rod 117 is attached to the inner sleeve 113, for example by a friction fit, using a pair of positioning screws 119. The inner sleeve 113 and the outer sleeve 115 are releasably held to one another by electromagnets 121. As shown in FIG. 9, perimeter magnets 121 are located on the inner surface 123 of the outer sleeve 115 and in the vicinity of the end 125 of the inner sleeve 113. Magnets 121 are also located on the inner sleeve 113 in the vicinity of the end 125. As would be known to one skilled in the art, the magnets on one surface may be replaced with a magnetic material—what is required is a magnetic field. A sensor 127 provides electronic feedback to signal when the magnetic field is broken. The force required to break the magnetic field is dependent upon the number of tips. For two tips, the force will be about 44N to about 36 N to about 22N, for three tips, about 66N, to about 54N to about 33 N and so on.

The rod 117 is resistant and optionally light transmitting. In one embodiment it is preferably an acrylic rod that functions as a light pipe. The rod 117 is preferably provided with light scattering segments (see FIG. 3 for equivalent structure 30). In the preferred embodiment, the light scattering segments are facets that provide rings of light spaced along the rod 117. Light scattering may be provided by etching or by machining or other methods as would be known to one skilled in the art. The distal end 116 also preferably scatters light. As shown in FIG. 1, an applicator 152 is attached to the distal end 116. In the preferred embodiment, the applicator 152 is in threaded engagement with the distal end 116, however, the applicator 152 and rod 117 may be a single unit or may be releasably attached to one another in any number of ways, as would be known to one skilled in the art. The applicator 152 retains the tips 114. As shown in FIG. 1, if additional strength is required, a slave 132 is placed in parallel with the shaft 112 (see FIG. 3 for equivalent structure 32 shown directly adjacent). As would be known to one skilled in the art, the features shown in FIGS. 4 and 5 may similarly be found in the rod 117.

Figure 10:
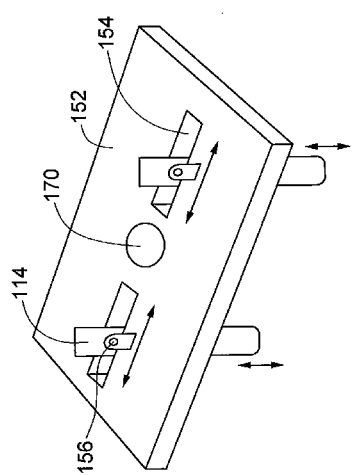
FIG. 10 is a perspective view of a tip in the applicator indicating directions of movement for adjustment.

As shown in FIG. 10 at least one of the tips 114 is adjustably located in apertures 154 in the applicator 152 to allow the practitioner to adjust the distance between the tips 114 prior to treatment i.e. orthogonal to the shaft. A rack and pinion or other suitable linear actuator allows for the adjustment. The tips do not approach one another or move away from one another during the treatment—they function to impart repetitive force impulses a set, but adjustable distance from one another. The tips 114 can also be adjusted proximally and distally using an adjustment screw 156. This allows the tips 114 to be placed accurately on the treatment location and to provide same force to the treatment area. The relative length of the tips 114 and the rod 117 is variable. The rod 117 may be shorter than the tips 114, the same length as the tips 114 or longer than the tips 114, thereby imparting variable force to the treatment area if the treatment area is flat, or the same force if the treatment area is contoured. An aperture 170 is for releasably retaining the distal end 116 of the rod 117, as described above.

Figure 11:
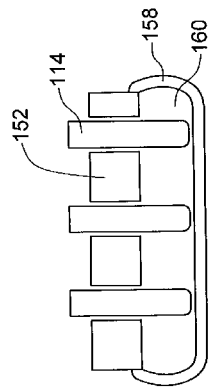
FIG. 11 is a longitudinal mid-section view of the applicator with a cover.
Figure 12:
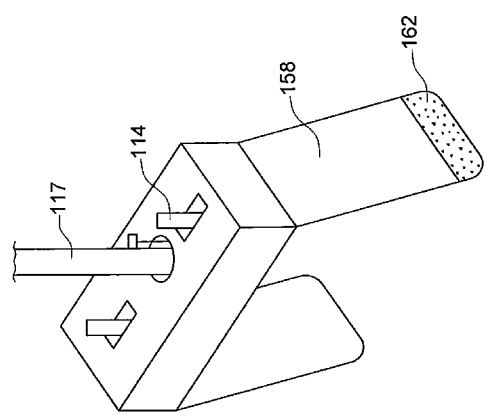
FIG. 12 is a perspective view of an alternative embodiment of the technology of FIG. 11.

As shown in FIG. 11, the tips 114 may be housed in a cover 158. The cover 158 may cover the entire tip 114 or part of the tips 114. A flexible layer 160, such as a gel or plastic polymer may be enveloped by the cover 158. This allows any force to radiate concentrically from the tips 114. As shown in FIG. 12, Velcro® or another suitable closure 162 allows the cover 158 to function as a wrap that can be placed around a joint or appendage.

Figure 13:
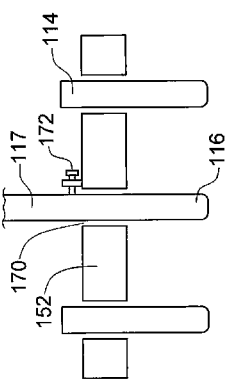
FIG. 13 is a longitudinal mid-section view of an alternative embodiment of FIG. 8.

In another embodiment, shown in FIG. 13, the applicator 152 is releasably located on the stylus 10 of FIGS. 1-5 such that the distal end 16 of the rod 17 extends through the applicator 152. In this embodiment, the applicator 152 has a central bore 170 for accepting the rod 17 and an adjustment screw 172 for releasably affixing the applicator 152 to the rod 117. Again, the tips 114 on the applicator can be adjusted laterally, proximally and distally, as shown in FIG. 12. The applicator 152 can be placed such that the distal end 116 of the rod 117 may impart force on the patient, or may transfer the force to the tips 114 via the applicator 152.

The foregoing is a description of the technology. As would be known to one skilled in the art, variations are contemplated that do not alter the scope of the technology. For example, feedback can be based on colour, intensity, light duration, colour sequence (flashing) or any combination thereof i.e. alternating colours. Light scattering may be effected by varying the light pipe diameter or by machining or etching or otherwise causing an alteration in the surface that results in light scattering. The light pipe, segments or distal end of the pipe may be emit light. If the light is visible at the end of the stylus, then the tip need not diffuse the light. The mechanism for allowing the stylus to collapse need not be confined to a magnetic field created by magnets on each of the outer and inner sleeve, but could, for example, be a magnetic field created by a magnet on one sleeve and a magnetic material on the other sleeve. Alternatively a friction fit could be employed.

Note that in the case of pulsed light audio feedback or vibration, a single colour, tone or vibration is all that is required to display either tension or compression ranges. In the case of audio feedback, the frequency of sound or other variants of sound could be used to indicate changes in measured force. Similarly, the frequency of vibration could be used to indicate changes in measured force.

While the foregoing is directed to a stylus, as would be known to one skilled in the art, any shape that can impart a force is contemplated, for example, paddles and hammers. Similarly, the force may be exerted by a cutting implement such as a scalpel or other medical device.

The invention claimed is:

1. A collapsible stylus for use in medical applications wherein a compressive force is applied at a treatment location, the stylus comprising:
    a light scattering tip at a distal end thereof;
    a strain gauge at a proximal end thereof;
    a shaft including an inner sleeve, an outer sleeve, and a light transmitting rod attached to the inner sleeve, the rod being partially housed within the inner sleeve and extending to the distal end of the stylus, the inner sleeve and the outer sleeve being releasably held to one another by a magnetic connection between at least one magnet on an inner surface of the outer sleeve and at least one magnet on the inner sleeve, the magnets being forced apart and the magnetic connection being broken in response to a predefined compressive force resulting in telescoping of the inner sleeve and the outer sleeve;
    a light source in communication with the rod; and
    a light controller in electric communication with the strain gauge and the light source, such that in use, a light signal, is emitted in a vicinity of the distal end, in response to a predefined force or a range of predefined forces.

2. The stylus of claim 1 wherein the strain gauge is a load cell.

3. The stylus of claim 2 wherein the light controller is a red green blue (RGB) controller.

4. The stylus of claim 1 wherein the rod is an acrylic light pipe.

5. A use of the stylus of claim 1 in a medical device for imparting a force.

6. The use of the stylus of claim 5, wherein the force is a repetitive compressive force.

7. The stylus of claim 1, further comprising a sensor which provides an electronic feedback to signal when the at least one magnet on the inner surface of the outer sleeve and the at least one magnet on the inner sleeve are forced apart and the magnetic connection is broken.

8. The stylus of claim 1 wherein the light source is a light emitting diode (LED).

9. The stylus of claim 1 wherein the rod has light scattering segments that are facets which provide rings of light spaced along the rod.

10. The stylus of claim 1, wherein the tip includes protrusions, dimpling or other surface contouring.

11. The stylus of claim 1, wherein the at least one magnet on the inner surface of the outer sleeve and the at least one magnet on the inner sleeve are electromagnets which are forced apart at a force of about 22 N.

12. The use of the stylus of claim 5, wherein the stylus collapses at a force of at least about 22 N when the at least one magnet on the inner surface of the outer sleeve and the at least one magnet on the inner sleeve are forced apart.

13. The use of the stylus of claim 12, wherein a sensor provides an electronic feedback to signal when the at least one magnet on the inner surface of the outer sleeve and the at least one magnet on the inner sleeve are forced apart and the stylus collapses.

* * * * *